United States Patent [19]

Adamowicz et al.

[11] Patent Number: 4,522,809

[45] Date of Patent: Jun. 11, 1985

[54] PROCESS FOR OBTAINING LIPID ENVELOPE VIRUS SUB-UNITS, NOTABLY ANTIGENS FOR USE AS VACCINES, THE PRODUCTS OBTAINED AND THEIR APPLICATIONS

[75] Inventors: Philippe Adamowicz, Garches; Ludwig Muller, Plessis Robinson, both of France

[73] Assignee: Institut Pasteur, Paris, France

[21] Appl. No.: 636,791

[22] Filed: Aug. 1, 1984

[30] Foreign Application Priority Data

Feb. 11, 1980 [FR] France ................................ 80 02978

[51] Int. Cl.³ ............................................ A61K 39/145
[52] U.S. Cl. ..................................... 424/89; 435/235; 435/236; 435/238; 435/239
[58] Field of Search .................. 424/89; 435/235, 236, 435/238, 239

[56] References Cited

U.S. PATENT DOCUMENTS

| 3,639,578 | 2/1972 | Batzer | 424/89 |
| 3,847,737 | 11/1974 | Kanarek | 424/89 |
| 4,199,450 | 4/1980 | Dulout et al. | 210/31 C |

FOREIGN PATENT DOCUMENTS

| 1587316 | 2/1970 | France . |
| 2248054 | 5/1975 | France . |
| 2422720 | 11/1977 | France . |
| 2475572 | 8/1981 | France . |

OTHER PUBLICATIONS

R. G. Webster et al., "Influenza Virus Subunit Vaccines . . . ", *Journal of Immunology*, 96, pp. 596-605, (1966).
B. A. Rubin et al., "Elicitation of Antibody Response . . . ", *Archiv. f. Virusforschung*, 20, H2, pp. 268-271, (1966).
A. R. Neurath et al., "The Effect of Nonaqueous Solvents on the Quaternary Structure . . . ", *Microbiol.*, 2, pp. 209-224, (1970), 7-8.
F. L. Ruben et al., "A New Subunit Influenza Vaccine . . . ", *Journ. Infectious Diseases*, 125, pp. 656-664, (1972).
H. Fukumi, "Production and Potency Standardization of Hemagglutinin . . . ", *Symp. Series Immunol.*, 20, pp. 99-105, (1973).
W. G. Laver et al., "Preparation and Immunogenicity of Influenza Virus . . . ", *Virology*, 69, pp. 511-522, (1976).
H. Bachmayer et al., "Preparation and Properties of a Novel Influenza Submit . . . ", *Postgr. Med. Journ.*, 52, pp. 360-367 (1976).
P. A. Gross et al., "Influenza Vaccine . . . ", *N.E. Journ. Med.*, 296, pp. 567-568, (1977).
M. Just et al., "A/New Jersey/76 Influenza Vaccine Trial . . . ", *Med. Microbiol. Immunol.*, 164, pp. 277-284, (1978).
M. L. Hammon et al., "Effective Protection Against Influenza . . . ", *Med. Journ. Aust.*, pp. 301-303, (1978).

*Primary Examiner*—Shep K. Rose
*Attorney, Agent, or Firm*—Frost & Jacobs

[57] ABSTRACT

A process is disclosed for producing virus sub-units with lipid envelopes, comprising, in a neutral or basic pH, dissolving a lower halogenated hydrocarbon, at a concentration equivalent to or approximating its limit of solubility, in an aqueous virus suspension, thereafter contacting, with stirring, the preparation so obtained with a nonionic detergent at a minimum concentration effective to induce disruption of virions into heavy sub-units for a length of time sufficient to permit said disruption, and in separating the heavy sub-units so obtained from the reaction medium. The process permits preparation of purified disrupted antigens for use as vaccines, notably influenza vaccines.

9 Claims, No Drawings

PROCESS FOR OBTAINING LIPID ENVELOPE VIRUS SUB-UNITS, NOTABLY ANTIGENS FOR USE AS VACCINES, THE PRODUCTS OBTAINED AND THEIR APPLICATIONS

This application is a continuation of application Ser. No. 466,581, filed Feb. 15, 1983, now abandoned.

The invention relates to the production of subunits of virus having lipidic envelopes bearing the surface antigens of the virus, and more particularly the production of antigens that can be used as vaccines. The process of the invention is of particular interest for the treatment of viruses, notably influenza viruses enabling obtention of vaccines containing subunits of influenza virus.

An influenza virus particle consists of genome with ribonucleic acids in conjunction with a nucleoprotein determining the specificity of its type which is surrounded by an inner protein membrane and an outer lipid membrane bearing glycoprotein spikes. The inner membrane is commonly known as the matrix protein (or matrix, or again, M protein), the lipid membrane is known as the envelope and the spikes fall into two distinct classes of glycoproteins called, respectively, neuraminidase (NA) and haemagglutinin (HA)

It is a well established fact that neuraminidase and haemagglutinin are the influenza virus antigens necessary to induce in man a good immunity against the disease. Consequently, all influenza vaccines should contain sufficient amounts of both these types of antigens.

Three types of vaccines with inactivated antigens may be considered to exist at present time.

The first type comprises antigens with intact virions. When innoculated to man this type of vaccine is known to induce undesirable reactogenic effects, due to the intact viral particles.

A second type of vaccine comprises virions that have been disrupted and the lipids partially extracted:the lipid membrane of previously purified virions is disrupted by the combined action of a lipid solvent, such as ether, and a detergent. In practice, lipid extraction is effected in a biphasic solvent-sample system requiring the use of 1 to 2 volumes of ether for one volume of virus preparation, and this operation may be repeated two or three times. The preparation so obtained contains HA and NA antigens and all the inner components of the envelope, and in addition it contains the detergent used. Although such a preparation therefore contains all the components of the virion with the exception of a portion of its lipids, this second type of vaccine is reputed to be less reactogenic than the first type.

Finally, a third type of vaccine consists solely of HA and NA glycoproteins; in practice, the previously purified virions are treated with a surfactant whereby only the spikes are detached from the virus nucleus constituted by the lipid envelope containing all the inner constituents of the virion, and this preparation is then subjected to zonal fractionnation by ultracentrifugation of the sample on a density gradient, the light fraction of the gradient containing the HA and NA antigens and the heavy fraction containing the nuclei. Owing to the fact that the HA and NA antigens are found in the light fraction of the gradient, it should be noted that the contaminating egg proteins, if any, and the detergent, are recovered in this fraction, this fact constituting a handicap for this type of vaccine. Finally, its immunogenic capacity is known to be weaker than that of the vaccine containing entire virions with equal amounts of HA and NA antigens, probably because said antigens have lost their original arrangement on the lipid envelope of the virion.

The above, briefly summarized indications, are given to situate the state of the art in the field of the invention. A certain number of bibliographical references illustrating the prior art will also be given. A recent article by Peter A. Gross and Francis A. Ennis is the New England Journal of Medicine, Mar. 10, 1977, Volume 296, No. 10, pages 567–568, compares the influenza vaccines prepared from intact viruses and those obtained from disrupted viruses. The bibliographical references accompanying this article also relate to the technique for manufacturing influenza vaccines.

The following are other, more specialized, articles:

R. G. Webster and W. G. Laver in "The Journal of Immunology", 1966, volume 96, No. 4, pages 596 et seq. "Influenza virus subunit vaccines; immunogenicity and lack of toxicity for rabbits of ether-and detergent-disrupted virus".

This article relates to an investigation into vaccines comprising viral subunits obtained by disruption with ether and detergents. It states that the treatment of mixoviruses with ether abolishes their pyrogenic activity although the resulting material remains antigenic in animals and humans. It adds that detergents will also induce disruption of virus particles and the liberation of haemagglutinating subunits. Detergents are considered to be less hazardous to manipulate than ether in the manufacture of vaccines. The authors have notably conducted investigations to determine whether influenza viruses disrupted or split with detergents were toxic for rabbits, and have compared quantitatively the immunogenicity of viral subunits with that of intact viruses and viruses treated with ether. The detergents used were sodium dodecyl sulphate and sodium deoxycholate.

The article by B. A. Rubin, W. A. Perzchala and A. R. Neurath "Elicitation of antibody response against influenza viruses by different viral subunit preparations" in Archiv. f. virusforschung, vol. 20 H2 pages 268 and seq. The authors investigate virus preparations obtained by treating viruses with combinations of "Tween" and ether or sodium deoxycholate, and subsequent purification of HA antigens by adsorption-desorption on red blood cells. The immunogenicity of the sodium deoxycholate-treated-HA antigen preparations was much lower than that obtained with Tween-ether-treated preparations.

The article by A. R. Neurath et al. in "Microbios" 1970, 7-8 209–224 volume 2, under the title "The effects of nonaqueous solvents on the quaternary structure of viruses:properties of haemagglutinins obtained by disruption of influenza viruses with tri-(n-butyl)phosphate" describes the disruption of influenza viruses with tri(n-butyl)phosphate (TNBP) in the presence of "Tween 80". The authors study the properties of haemagglutinins obtained after disruption and observe that these HA haemagglutinins ressemble those obtained by treatment with diethyl ether. However, TNBP is much less detrimental to neuraminidase of the B/Mass type virus than ether.

The article by Frederick L. Ruben and George Gee Jackson in "The Journal of Infectious Diseases" vol. 125 No. 6 June 1972 pages 656 to 664 under the title "A new subunit influenza vaccine. Acceptability compared with standard vaccines and affects of dose on antigenicity" reports work on influenza viruses disrupted with tri-(n-butyl)phosphate. The authors report good acceptability of the preparations obtained and reduced pyrogenic reactions following administration.

The article by H. Fukumi in the report of the "International Symposium on Influenza Vaccines for Men and Horses", London 1972, Symp. Series Immunobiol. Standard Vol. 20, pp. 99–105 (Karger, Basel/Munchen/Paris/London/New York/Sydney 1973) under the title "Production and Potency standardization of haemagglutinin sub-unit influenza vaccine" investigates the sub-units obtained by ether treatment of intact influenza viruses.

The article by W. G. Laver and R. G. Webster in "Virology 69" 511–522 (1976) under the title "Preparation and immunogenicity of an influenza virus haemagglutinin and neuraminidase subunit vaccine" reports the preparation of an influenza virus by treatment with ammonium deoxycholate. Other detergents, such as sodium dodecyl sulphate and Triton X-100 are also mentioned. The authors observed that ammonium deoxycholate provided a disrupted virus particle vaccine wherein the haemagglutinin and neuraminidase were as effective as the intact inactivated virion vaccine.

The article by H. Bachmayer et al. in "Postgraduate Medical Journal" (June 1976) Vol. 52, pages 360–367 under the title "Preparation and properties of a novel influenza subunit vaccine" describes the selective solubilization of haemagglutinin and neuraminidase from intact influenza virus particles by means of a cationic detergent, CTAB (cetyltrimethyl ammonium bromide). They established that the solubilization procedure did not alter the immunogenic properties of the two antigens HA and NA. These trials are confirmed and completed by M. Just et al. in Medical Microbiology and "Immunology 164,277–284(1978) under the title "A New Jersey/76 Influenza Vaccine Trial in Seronegative School children, Comparison of a Sub-unit Vaccine with a Whole-Virus Vaccine". This article compares the properties of the whole-virus vaccine with the sub-unit vaccine obtained by the H. Bachmayer et al procedure.

The article by M. Leigh Hammond et al. in Med. J. Aust 1978,1:301–303 "Effective protection against influenza after vaccination with subunit vaccine" reports a clinical trial on the results of vaccination against influenza.

The above-mentioned articles also contain numerous bibliographical references that the one skilled in the art can consult if needs be. These elements of the prior art reveal a practically unanimous in favour of the value of vaccines containing disrupted virion particles or HA and NA subunits. However, all research workers endeavour to perfect the widely known technique for disrupting virions, notably by finding disruption reagents that are easier to manipulate and enable more efficient steps to be taken subsequently to eliminate the secondary products that are often responsible for undesirable reactogenicity when the vaccine is administered.

The object of the present invention is such an improved process for the production of purified antigens for use as vaccines, notably as a subunit influenza virus vaccine. The improved results are obtained, according to the invention, by means of a disrupting reagent consisting of a combination of means.

More precisely, the present invention relates to a process for the controlled disruption of virions which results in the freeing of heavy fragments of the virus envelope bearing the HA and NA glycoprotein spikes, followed by their concentration by conventional fractionnation methods adapted to very high molecular weight compounds. It will be noted that according to the invention the production of heavy immunogen sub-units enables them to be separated from the light components, notably from the detergent or solvent used, and from the egg proteins, if present in the initial sample so treated, as well as from a portion of the non-immunogenic components of the virion. Furthermore, as these subunits are smaller and less rigid than the intact virion, they can be filtered on a sterilizing membrane, such as a membrane of 0.22 micron porosity, thus practically ensuring that the antigen preparations obtained according to the invention are practically perfectly sterile.

A further object of the invention is the products so obtained, and particularly purified virus subunits that can advantageously be used for the preparation of vaccines, such as influenza vaccine. It relates to all the pharmaceutically acceptable forms, and notably to aqueous and lyophilized preparations and injectable solutes.

Still another object of the invention is the application of the products so obtained, especially of the purified viral antigens that retain their immunogenic properties.

In its most general form, the process of the present invention for obtaining particles of the lipid envelopes of viruses consists in carrying out the following steps in the order given, at a neutral or basic pH:

(1) in dissolving a lower halogenated hydrocarbon, such as chloroform, at a concentration equivalent to or approximating its limit of solubility, in an aqueous virus suspension, (2) in contacting, under stirring, the preparation so obtained with a nonionic detergent at the minimum effective concentration to cause disruption of the virions into heavy subunits for a length of time sufficient to produce the said disruption.

(3) in separating the heavy subunits so obtained from the reaction medium.

In the process of the invention for producing purified lipid envelope virus subunits, particularly antigens for use as vaccines, by the general technique of virion disruption method followed by purification to concentrate and isolate viral envelope subunits, virion disruption is effected in a monophasic reaction system, at a neutral or basic pH, by means of a nonionic detergent and a halogenated lower hydrocarbon, the latter being used at a concentration equal to or approximating its limit of solubility in water. The halogenated lower hydrocarbon used in the invention must be such that its use in no way causes the final product to be toxic. Chloroform may be mentioned as an example of a suitable lower halogenated hydrocarbon. The following detailed specification will be made with reference to chloroform while in no way limiting the scope of the invention to this particular lower halogenated hydrocarbon.

The applicant has discovered that the combined action of a nonionic detergent, such as polysorbate 80, and a lower halogenated hydrocarbon, such as chloroform, at a concentration equal to or approximating its limit of solubility in water, was sufficient to split the lipid envelope and to solubilize a very small portion of it so that practically all the HA and NA antigens are carried on heavy subunits of the lipid envelope, thus allowing their quantitative separation by a suitable fractionnation step. It should be noted that the system used is a monophasic system that does not require the separation of two nonmiscible solvent-water phases; the preparation of disrupted antigens can thus be used directly for the subsequent fractionnating step.

According to the process of the invention, the operation is effected with a neutral or basic pH, for example a pH in the range of about 7.5 to 8.7. Generally speaking, the pH of the reaction medium is adjusted after dissolution of the chloroform. However, the pH of the starting viral suspension can also be adjusted. This adjustment of pH is effected by any suitable conventional means.

According to one embodiment of the process of the invention, a further amount of chloroform can be added after the addition of the nonionic detergent if the pH of the reaction mixture is basic.

It should be noted that the order of the steps of the process is critical to obtain a monophasic reaction system and that it is indispensable to solubilize the lower halogenated hydrocarbon in the virus suspension before adding the nonionic detergent. The addition of chloroform to a polysorbate 80 solution was observed to precipitate the detergent, so it was impossible to obtain a monophasic reaction system.

As above mentioned, an excess of chloroform may be added, but this further addition can only be effected with a basic pH. When operating under such conditions the reaction system remains monophasic and precipitation of detergent therefore does not occur. Chloroform saturation can thus be ensured without modifying the concentration of the detergent.

As it was previously mentioned, the process of the invention can be used to treat viruses with lipid envelopes, and more especially influenza viruses. Among the viruses that can be treated by the process of the invention mention may be made, notably, of viruses that can provide subunit vaccines, containing surface antigens carried by subunits of the lipid envelope, such as the following viruses: Togavirus, Rhabdovirus, Leukovirus, Coronovirus, Adenovirus, the virus of herpes, vaccine virus, and the virus of type B hepatitis (DANE particles), which are all viruses accessible to the man of the art.

The raw material used in the process of the invention consists of a suspension of one of the above-mentioned viruses obtained by conventional methods, with the only proviso that the contamination by lipids that are not constituents of the virion be moderated so that the chloroform is not excessively consumed by these lipids. A suspension of influenza virus grown on eggs and concentrated and/or multiplied by conventional methods can be used for example.

According to the invention, any nonionic detergent can be used.

As a suitable nonionic detergent preference is given to a surfactant containing polyoxyethylenic derivatives of partial esters of fatty acids and hexitol anhydrides derived from sorbitol, and especially the product available under the trade name "Tween 80" which is a polyoxyethylene (20) sorbitanne monoleate also known as polysorbate 80.

Among the other nonionic detergents suited to the requirements of the invention may be mentioned:

(1) condensates of alkylphenols and ethylene oxide
(2) addition products of aliphatic ethers and ethylene oxide
(3) addition products of ethylene esters and oxides
(4) addition products of amines and ethylene oxide
(5) addition products of alcanolamides and ethylene oxide.

In this connection, reference may be made to French Pat. No. 74 35 179 published under No. 2.248.054 in which examples of such suitable nonionic agents are given.

As stated above, the nonionic detergent is used at the minimal concentration effective to cause disruption of virions into heavy subunits. It will be easy for a man skilled in the art to effect routine trials to determine the concentration of a given nonionic detergent that should be used. When the nonionic detergent is polysorbate 80, the minimum effective concentration is in the range of 0.02 to 0.2%.

The chloroform-virus suspension should remain in contact with the nonionic detergent for a sufficient period to enable the viral disruption to occur. Generally speaking, the duration of contact lies in the range of 1 to 20 hours. The temperature of the reaction medium is not critical, but it must not be such as to cause denaturation of the virion being treated. It is generally convenient to operate at +4° C.

As stated above, the chloroform is used at a concentration equivalent to, or approximating, its maximum degree of solubility in the aqueous medium. This concentration advantageously lies in the range of 0.4 to 0.7% by volume/volume.

Advantageously, the chloroform can be added to the virus suspension by exclusion chromatography in a 0.5% chloroform buffer, exclusion chromatography being effected, for example, according to the procedure described in French Pat. No. 77 12 518. Thus, at the same time as the addition of chloroform to the raw material, a very high degree of pre-purification of the same is obtained.

As previously stated, the process of the invention is particularly well suited to the treatment of influenza virus to obtain virus subunits for the manufacture of influenza vaccines, and in this case the preferred detergent is polysorbate 80.

Thus, according to a preferred embodiment, the process of the invention consists:

(1) in adding chloroform at a concentration of between about 0.4 and 0.5% (volume/volume) to an influenza virus suspension;

(2) in adding a nonionic detergent, such as polysorbate 80 at a concentration in the range of about 0.02 to 0.2%, when the chloroform is completely dissolved and after adjusting the pH to a value of between 7.5 and 8.7;

(3) in stirring the resulting reaction medium which is in the form of a monophasic system for 1 to 20 hours;

(4) in purifying the disrupted virion preparation;

According to another embodiment, the process consists:

(1) in adding chloroform at a concentration in the range of about 0.4 to 0.5 (volume/volume) to an influenza virus suspension;

(2) in adding a nonionic detergent, such as polysorbate 80 at a concentration of between about 0.02 and 0.2%, when the chloroform is completely dissolved and after adjusting the pH to a value of between 8 and 8.7;

(3) in adding an additional amount, of up to 0.2%, of chloroform;

(4) in stirring the resulting reaction medium, in the form of a monophasic system, from 1 to 20 hours;

(5) in purifying the preparation of disrupted virions.

According to another preferred embodiment of the process of the invention, an inactivation agent such as formaldehyde or β-propiolactone (β-PPL) is added to the reaction medium at any time during the process, taking care, however, that the neutral or basic pH of the reaction medium is maintained. The inactivation agent is preferably added after the nonionic detergent, If β-propiolactone is used as inactivation agent, care should be taken to adjust the pH of the reaction medium by the addition of a base, by suitable means, to avoid a drop in the pH due to an autohydrolysis of the inactivation agent. The inactivation agent, such as formaldehyde or β-propiolactone (β-PPL) is used at the usual concentrations to obtain the inactivation effect. Generally, β-propiolactone or formaldehyde are used at a concentration of about 0.02%.

The reaction medium obtained after step (2) of the process of the invention is then subjected to a fractionnation step to separate the heavy subunits from said medium. This step is a fractionnation step adapted to the purification of heavy molecular weight compounds. According to the invention, two industrially applicable systems of purification may be used:

(1) the first system consists in a separation by zonal ultra-centrifugation on a density gradient; it will be preferably choosen a sucrose gradient dynamically self-formed in a type K2 reorientation rotor (Electronucleonics) with a continuous input sample flow. The haemagglutinin and neuraminidase activities are observed in the dense fractions of the gradient, whereas the light layers and the effluent contain the chloroform and polysorbate 80, the nonimmunogenic components resulting from virion disruption and the egg proteins that may have been present in the sample treated.

The fractions containing the immunogens are collected and the mixture is diluted in a physiological salt solution; a sterilizing filtration through membranes with 0.22 micron porosity finishes antigen preparation.

(2) the principle of the second system of separation is the one applied to the purification of influenza virus as described in French Pat. No. 77 12 518 and its French patent for addition No. 78 10 769.

The principle of this system of separation is a liquid phase exclusion chromatography on porous silica beads, preferably with a mean porous diameter of 60 nanometers and a size of 100 to 200 microns. The adsorbent sites of the silica are previously blocked by passing through them an aqueous solution of a polyoxyethylene agent, such as polyethylene glycol 20,000; it will be noted that this passivation of silica is not deteriorated by repeated passages of the sample to be fractionnated which, on the contrary, at each injection supplies an additional charge of the polyoxyethylene agent in the form of the polysorbate 80 it contains, which can only reinforce the original passivation. The chromatography buffer is a buffered salt solution, preferably at pH 8.0–8.2 and containing 0.5% chlorofrom, that is used here as an atiseptic in order to guarantee perfect sterility during the operations.

The chromatographic apparatus is provided with automatic devices permitting continuous operation, the preparation of antigens to be fractionnated being injected at regular intervals, the respectively excluded and delayed phases at the column outlet being distributed into separate containers by electrovalves controlled by a programmer.

The excluded phase contains the antigens with haemagglutinin and neuraminidase activities in the chloroform buffer, whereas the delayed phase contains the polysorbate 80 and the nonimmunogenic components resulting from the disruption of virions and any egg proteins in the treated sample.

The preparation of antigens purified in this way is depleted of chloroform by evaporation in partial vacuum, then dialyzed by diafiltration with a buffered physiological salt solution, and finally filtered through sterilizing membranes with 0.22 micron porosity.

In all cases, the process of the invention leads to the production of lipoglycopeptide structures of high molecular weight with a composition and structure very similar to those of the virion envelope. Their immunogenicity is therefore similar or equivalent to that of the entire virion.

Following purification of the disrupted virion preparation, the process of the invention makes it possible to recover a preparation with a protein concentration that may contain up to half the amount of proteins and lipids as the initial preparation for an equal amount of antigenic activity.

The invention presents many advantages for the preparation of purified antigens for use as vaccines, notably in its application to the influenza vaccine. For the conditions of the disruption reaction, the process of the invention first uses a monophasic reaction system because chloroform is used in an amount very close to its maximum concentration of solubility in water.

In the conventional systems of the prior art, such as Tween-ether systems, the reaction mixture is biphasic and the subunits released are not all of high molecular weight, which does not allow quantitative separation of antigens by a single fractionnation step.

According to the invention, on the contrary, it is possible then simply to purify the viral suspension owing to the relatively large dimension of the antigen obtained. It is thus possible to eliminate contaminants: Tween, chloroform, proteins contaminating the medium, lipids, as well as a portion of the virus disruption products. In the techniques of the prior art, both the detergent used and the virus disruption products remain in the virus preparation. The process of the invention provides a much higher level of deproteinization, whereas in the known technique it was impossible to purify the split antigens with a satisfactory yield.

Furthermore, the disrupted antigen can be made sterile by filtration through a sterilizing membrane. Any dead bacteria which may have grown in an influenza virus culture medium are, therefore, eliminated, thus eliminating a risk of reactogenicity when the vaccine is administered for example. In whole-virus vaccines, the viral suspension is usually sterilized by ultra-violet rays. The bacteria which may be present in the suspensions sterilized in this manner may be responsible for reactogenic effects when the vaccine is used.

The following examples illustrate the present invention while in no way limiting its scope. The process is more particularly applied to influenza virus grown in eggs, concentrated and/or purified by known methods. The in vitro methods for antigen assays were haemagglutination or radial immunodiffusion in gelose containing a pure anti-haemagglutinin serum (Schild et al. 1972, Journal of General Virology 16,231,236) (J. Biol. Chem. 234, 1959, p.1971) for the detection of neuraminidase.

EXAMPLE 1

Influenza virus was grown on embryonic chicken eggs at +34.5° C. for two to three days. The eggs were cooled to +4 ° C. overnight and the infected allantoic fluids were collected and clarified by centrifugation.

The virions of the allantoic fluid were then adsorbed on chicken erythrocytes and then desorbed by the techniques known to the man skilled in the art, and the virulent liquor thus obtained was finally concentrated by ultrafiltration. 0.5% of chloroform was added to this virulent concentrate then, after dissolution of the solvent, the pH was adjusted to 8.2, and 0.1% of polysorbate 80 was then added; the mixture was stirred at +4° C. overnight and then clarified by centrifugation, after which it was injected at a rate of 12 l/h into a K2 rotor (Electronucleonics) rotating at 3500 r.p.m. and containing a sucrose gradient (2 to 55%). After the whole sample has been treated, the rotor was decelerated under known conditions that permit an adequate reorientation of the gradient. After the rotor had been stopped its contents were syphoned off from below and 100 ml fractions were collected. The gradient fractions, generally with 20 to 45% sucrose, containing the HA and NA antigens, were collected and the mixture was dialyzed by diafiltration with a buffer physiological salt solution and, finally, the antigen suspension was filtered through sterilizing membranes with 0.22 micron porosity.

EXAMPLE 2

The same procedure was used as in example 1, except that the β-PPL was added at a concentration of 0.02% after the addition of Tween-80 and that the pH was adjusted to 8.2 by the addition of a base.

EXAMPLE 3

The same procedure was used as in example 1, except that the pH of the virulent chloroform-containing concentrate was adjusted to pH 8.7 and that the β-PPL was added at a concentration of 0.02% after the addition of polysorbate 80; during autohydrolysis of β-PPL, the pH decreased progressively to pH 7.6-7.7 and was readjusted to pH 8.2 by the addition of a base before the purification step.

EXAMPLE 4

The same procedure was used as in example 1, except that formaldehyde was added at a concentration of 0.02% after the addition of polysorbate 80.

EXAMPLE 5

0.5% of chloroform was added to the virulent concentrate obtained as described in example 1; after dissolution of the chloroform, the pH was adjusted to 8.2, then polysorbate 80 was added at a concentration of 0.1%; the mixture was maintained under magnetic stirring overnight and was then clarified successively by centrifugation and by filtration through membranes of 0.45 micron porosity. The antigen preparation so obtained was subjected to a fractionnation step by exclusion chromatography on porous silica beads in a 0.5% chloroform buffer, pH 8.2. The chloroform was removed by vacuum evaporation from the excluded fraction containing the HA and NA antigens, which was then dialyzed by diafiltration with a buffered normal salt solution and finally filtered through sterilizing membranes of 0.22 micron porosity.

EXAMPLE 6

The same procedure was used as in example 5, except that the β-PPL was added as described in example 2.

EXAMPLE 7

The same procedure was used as in example 5, except that the β-PPL was added as described in example 3.

EXAMPLE 8

The same procedure was used as in example 5, except that formaldehyde was added as described in example 4.

EXAMPLE 9

A vaccine was prepared by mixing the antigen preparations so obtained from each virus strain recommended by the WHO and corresponding to the epidemiological situation obtaining, and by adjusting their concentration either in international units of haemagglutinin, or in micrograms of haemagglutinin, in a volume of 0.5 ml in a physiological saline solution buffered at pH 7.3 and containing sodium ethyl mercurithiosalycilate at a concentration lower than or equivalent to 1/10 000. The efficacy of this type of vaccine has been proved on man.

For example, a trivalent vaccine was prepared in this manner from monovalent antigens disrupted and purified according to the invention by mixture and dilution with the vaccine dilution buffer to obtain, in 0.5 ml of final mixture:

300 IU of type A/USSR/$H_1N_1$
500 IU of type A/TEXAS/$H_3N_2$
400 IU of type B/HK.

56 adult subjects, taken from the active population, received one dose (0.5 ml) of the vaccine by the subcutaneous route. Serological tests were effected by taking blood samples on the day of vaccination and 30 days later. Assays of antibodies inhibiting haemagglutinin were effected for the 3 antigens according to the method recommended by the WHO. The seriological conversion rates and the geometric averages of antibody titers before and after vaccination were calculated; the results are given in the table below and show the good immunogenecity of this type of vaccine.

|  | A/USSR/$H_1N_1$ | A/TEXAS/$H_3N_2$ | B/HK |  |
| --- | --- | --- | --- | --- |
| Seroconversion rates | 92.8% | 91.0% | 89.3% |  |
| Geometric average of antibodies | 4.4 | 3.9 | 6.0 | before vaccination |
|  | 183 | 27 | 109 | after vaccination |

As a result of this study, it may be concluded that this vaccine has good tolerance as it only gave rise to a very few benigh post-vaccinal reactions.

EXAMPLE 10

In order to demonstrate the higher level of purification obtained with the process of the present invention, the first step of the invention process was effected by emulsion chromatography in 0.5% (vol./vol.) chloroform buffer according to the process described in French Pat. No. 77 12 518, of a virulent concentrate as defined in example 1. A highly purified virus preparation (Do) was thus obtained containing 0.5% chloroform. The pH of this preparation was then adjusted to 8.7; 0.1% polysorbate 80 was then added, followed by 0.02% β-propiolactone.

The mixture so obtained was stirred for 18 hours after which the pH was adjusted to 8.2 by the addition of a suitable base.

The preparation of disrupted antigens so obtained was subjected to fractionnation by zonal centrifugation on a sucrose gradient under the conditions indicated in example 1.

The consecutive steps of examples were applied to obtain the preparation of purified disrupted antigens (D). This protocol was applied to three layers of influenza virus corresponding to the epidemiological situation in Europe in the period 1978-1979.

Virus A/USSR/H$_1$N$_1$
A/TEXAS/H$_3$N$_2$
B/HK.

For each purified virus preparation (D$_o$) on the one hand, and for each purified disrupted antigen preparation (D) obtained according to the process of the invention on the other, the haemagglutinin activity (expressed in international units IU) and the protein and phospholipid concentrations were determined and the specific activities IU/mg of proteins (Table I) and the IU/nM of phospholipids (Table II) were calculated.

The results of tables I and II show that the purified preparations (D) obtained by the process of the invention have a haemagglutinin antigen level higher than that of highly purified virus preparations (D$_o$) for equal quantities of proteins and phospholipids.

TABLE I

| | Specific activity in IU/mg proteins | | |
|---|---|---|---|
| | A/USRR/H$_1$N$_1$ | A/TEXAS H$_3$N$_2$ | B/HK |
| Do | 9 245 | 8 957 | 24 980 |
| D | 15 584 | 15 131 | 42 256 |
| D/Do | 1.69 | 1.69 | 1.69 |

TABLE II

| | Specific activity in IU/nM phospholipids | | |
|---|---|---|---|
| | A/USSR/H$_1$N$_1$ | A/TEXAS/H$_3$N$_2$ | B/HK |
| Do | 61 | 45 | ND |
| D | 139 | 121 | 533 |
| D/Do | 2.3 | 2.7 | ND |

ND: not determined
Do: highly purified virus preparations obtained by exclusion chromatography.
D: purified split antigen preparations obtained by the process of the invention.

What we claim is:

1. A process for the production of immunogenic heavy subunits of influenza virus, comprising the following steps, carried out at a neutral or basic pH:
   (1) dissolving an amount of chloroform in an aqueous influenza virus suspension to obtain a concentration of chloroform equivalent to or approximating its solubility limit in said suspension, thereafter,
   (2) adding, with stirring, to the preparation so obtained a nonionic detergent while maintaining a single phase system, said detergent being added at the minimal concentration necessary to effect disruption of the virus into heavy immunogenic subunits, and stirring this mixture for a sufficient length of time to obtain said disruption, said heavy subunits comprising neuraminidase and hemagglutinin antigens in their original arrangement attached to fragments of the lipid envelopes of said virus, and
   (3) separating the heavy subunits so obtained from lighter components by applying gradient fractionation methods to the reaction mixture, said lighter components comprising said chloroform, said detergent and other products originating from the disruption of said virus, and said heavy subunits being in the dense fraction of the gradient, wherein an inactivation agent is added to the reaction medium at any time during the process.

2. Process according to claim 1, which comprises the following steps:
   (1) dissolving said chloroform to obtain a concentration of about 0.4 to 0.7% (volume/volume),
   (2) adding said nonionic detergent to obtain a concentration in the range of about 0.02 to 0.2% and stirring the reaction medium, at a pH between about 7.5 and about 8.5 for 1 to 20 hours, and
   (3) separating the immunogenic heavy subunits of the influenza virus.

3. Process according to claim 1 for obtaining a preparation of purified disrupted antigens of influenza virus, which comprises the following steps of:
   (1) adding said chloroform at a concentration of between about 0.4 and 0.5% (volume/volume) to influenza virus suspension;
   (2) adding, when the chloroform is completely dissolved and after adjusting the pH to a value of between 8 and 8.7, said nonionic detergent at a concentration of about 0.02 to 0.2%,
   (3) adding an additional amount of chloroform of up to 0.2%,
   (4) stirring the resulting reaction mixture, which is in the form of a monophasic system, for 1 to 20 hours, and
   (5) in purifying the preparation of split virions.

4. Process according to claim 1, wherein the inactivation agent is β-propiolactone and it is added after the addition of the nonionic detergent at a rate of about 0.02%.

5. Process according to claim 1, wherein said aqueous suspension of influenza virus is obtained from an allantonic solution of influenza virus which, after its preparation, is subjected in a known manner to adsorption-elution steps on erythrocytes, then clarification by centrifugation and filtration, thus providing a concentrate containing the virion, which is used to form the aqueous solution as starting material.

6. Process according to claim 1 wherein said nonionic detergent is a surfactant containing polyoxyethylenic derivatives of partial esters of fatty acids and hexitol anhydrides derived from sorbitol.

7. Process according to claim 1, wherein said nonionic detergent is selected from the class consisting of:
   (1) condensates of alkylphenols and ethylene oxide;
   (2) addition products of aliphatic ethers and ethylene oxide;
   (3) addition products of esters and ethylene oxide;
   (4) addition products of amines and ethylene oxide;
   (5) addition products of alkanolamides and ethylene oxides.

8. A process according to claim 1, wherein an additional amount of chloroform up to the amount of step (1) is added after said nonionic detergent to the reaction medium at a pH between about 8 and 8.7.

9. A process according to claim 8, wherein said chloroform is in an amount up to 0.2% (volume/volume) of the reaction medium.

* * * * *